United States Patent [19]

Schmitt

[11] 4,120,917
[45] Oct. 17, 1978

[54] PROCESS FOR PREPARING TERTIARY ALKYLPHOSPHORODICHLORIDITES

[75] Inventor: Kirk D. Schmitt, Pennington, N.J.

[73] Assignee: Mobil Oil Corporation, New York, N.Y.

[21] Appl. No.: 782,271

[22] Filed: Mar. 28, 1977

[51] Int. Cl.² ............................................. C07F 9/146
[52] U.S. Cl. .................................... 260/976; 260/960
[58] Field of Search ............................... 260/960, 976

[56]  References Cited

U.S. PATENT DOCUMENTS 3,309,431   3/1967   Olivette et al. ................... 260/976

OTHER PUBLICATIONS

Eliseenkov et al., "Chem. Abs.", vol. 64, (1966), 11074–11075.
Abramov et al., "Chem. Abs.", vol. 51, (1957), 15440–15441.

*Primary Examiner*—Anton H. Sutto
*Attorney, Agent, or Firm*—Charles A. Huggett; Raymond W. Barclay; Thomas S. Szatkowski

[57]  ABSTRACT

Tertiary alkyl phosphorodichloridites, characterized by the formula:

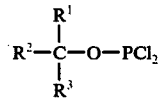

where $R^1$, $R^2$ and $R^3$ may be alkyl having from about 1 to about 4 carbon atoms, aryl having from about 6 to about 8 carbon atoms, or aralkyl having from about 7 to about 10 carbon atoms, however, at least one of $R^1$, $R^2$ and $R^3$ must be alkyl, as new compounds, and synthesis thereof by reacting, at temperatures of 0° C or less, a tertiary alcohol, a tertiary amine scavenger, and phosphorus trichloride, the $PCl_3$ being employed in amounts in excess of the stoichiometric amount needed to react with the alcohol are provided. Both chlorines of the tertiary alkylphosphorodichloridites so produced may be relaced by $RX^-$ groups from alcohols (ROH), thiols (RSH), or amines ($RR^6NH$) in order that trisubstituted phosphite compounds of the formula:

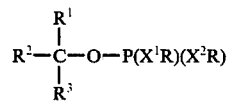

are produced. Disubstituted phosphorus acids of the formula:

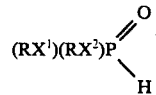

may be produced by heating the trisubstituted phosphite compounds. The $RX^-$ groups are retained as the substituents of the phosphorus acid compounds. Such phosphorus acids are extremely useful in lubricating media as antiwear agents, in insecticides and as additives in rubber.

6 Claims, No Drawings

PROCESS FOR PREPARING TERTIARY ALKYLPHOSPHORODICHLORIDITES

BACKGROUND OF THE INVENTION

1. Field of the Invention

The invention relates to tertiary alkylphosphorodichloridite and derivatives thereof, including synthesis of such compounds which are further utilized in the synthesizing of compounds such as derivatives of phosphorus acid.

2. Description of the Prior Art

"Organophosphorus Compounds" by G. M. Kosolapoff, published by John Wiley & Sons, Inc. (1950), discloses, on page 180, that compounds of the general class $ROPCl_2$ are obtained by the addition of the appropriate alcohol to a moderate excess of the stoichiometric amount of the phosphorus trichloride needed to react with the alcohol. Excess phosphorus trichloride is used to suppress the continued substitution of the chlorine atoms of the $ROPCl_2$ with $RO^-$ groups. Thus, the overall reaction may be represented by the formula:

$$ROH + PCl_3 \rightarrow ROPCl_2 + HCl \quad (A)$$

However, when the R group is aliphatic, the reaction is subject to complications which depend on the structure of the alcohol used. Thus, while primary and secondary alcohols yield desired dichlorophosphites, tertiary alcohols yield undesirable alkyl chlorides.

Articles by Gerrard et al., *J. Chem. Soc.* 1953, p. 1920, and Fertig et al., *J. Chem. Soc.* 1958, p. 1488 show unsuccessful attempts at forming dichlorophosphites from tertiary alcohols. Gerrard reported that all attempts to form the tertiary alkylphosphorodichloridite by the interaction of phosphorus trichloride and a tertiary alcohol failed.

Also, in the Kosolapoff book, p. 184, it is shown that the reaction of dichlorophosphites with 1 mole of an alcohol in the presence of an equivalent of a tertiary base is the best preparation available for dialkyl chlorophosphites:

$$ROPCl_2 + ROH + Base \rightarrow (RO)_2PCl + Base \cdot HCl \quad (B)$$

Mark et al., in *J. Organic Chemistry, Vol.* 29, p. 1006 (1964), show the formation of compounds having the formula:

$$(t-C_4H_9O)_2P(O)H$$

via the thermal decomposition of tri-t-butylphosphite, viz,

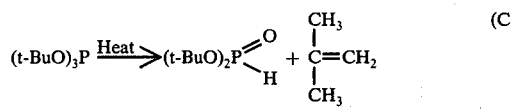

(C)

SUMMARY OF THE INVENTION

It has now been found that tertiary alkylphosphorodichloridites can be obtained in a high state of purity and good yield by reacting a tertiary alcohol, tertiary amine scavenger and excess phosphorus trichloride at temperatures of 0° C. or less. This reaction may be illustrated as follows:

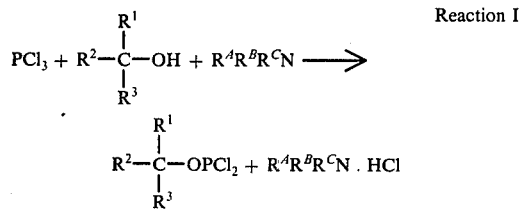

Reaction I

The tertiary alcohol utilized in the above reaction is represented by the formula:

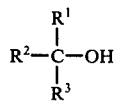

where $R^1$, $R^2$ and $R^3$ may generally be alkyl, aryl, or aralkyl, however, at least one of $R^1$, $R^2$ or $R^3$ must be alkyl. It is preferred that the $R^1$, $R^2$ and $R^3$ groups which are alkyl have from about 1 to about 4 carbon atoms; that the groups which are aryl have from about 6 to about 8 carbon atoms; and that the groups which are aralkyl have from about 7 to about 10 carbon atoms. It is most preferred that the $R^1$, $R^2$ and $R^3$ groups be chosen from the groups methyl, ethyl, propyl, butyl and phenyl. Thus, tertiary alcohols such as t-butanol, t-amyl alcohol, 3-methyl-3-hexanol and 2-phenyl-2-propanol, are particularly preferred.

The function of the tertiary amine in this reaction is to act as a scavenger and thus prevent the HCl formed by the reaction of the $PCl_3$ and the alcohol from attacking the tertiary alcohol. In this regard, it is important that a tertiary amine be present to prevent the formation of unwanted alkyl chlorides, however, the particular tertiary amine used is not important. Secondary or primary amines cannot be used for this application since their reaction with $PCl_3$, i.e., $R_2NH + PCl_3 \rightarrow R_2NPCl_2 + HCl$ produces additional deleterious HCl, thus contributing to, rather than solving the problem of formation of unwanted alkylchlorides. The tertiary amine utilized in reaction I may be generally described as a tertiary aliphatic or aromatic amine which has the formula:

$$R^A R^B R^C N$$

where $R^A$, $R^B$ and $R^C$ are alkyl or aryl. Preferred are those amines where the alkyl or aryl groups contain from about 2 to about 16 carbon atoms. Amines in which the alkyl groups are cyclic are also contemplated. Additionally, pyridine and its derivatives, such as substituted pyridine; quinoline and its derivatives, such as substituted quinoline; and amines having the formula:

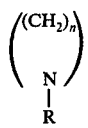

where $n$ is 4 or 5 and R is alkyl or aryl containing from 1 to about 16 carbon atoms are suitable. Diethylaniline is particularly contemplated.

In carrying out Reaction I, it is important that phosphorus trichloride in excess of the stoichiometric amount needed to react with the alcohol be used to prevent further substitutions of the chlorine atoms of the alkylphosphorodichloridites with

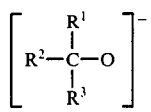
5 groups. This excess may suitably be from about 1.25 to 4 moles of the $PCl_3$ per mole of tertiary alcohol; with from 2 to 3 moles/mole being preferred. The molar ratio of the amine to the alcohol is generally maintained at 1:1. Higher ratios, i.e., amine/alcohol > 1, can be used if desired but are not necessary while lower ratios should be avoided since the amount of amine would be insufficient to reduce the undesirable side reaction with HCl.

The alcohol is added slowly to the excess $PCl_3$, which may be dissolved in a suitable solvent such as: pentane, petroleum ether, ethylether, benzene, toluene, hexane, mineral oils or other non-volatile solvents, if the ultimate use of the product will not be affected by the presence of these solvents. The reaction must be carried out in the absence of water, otherwise hydrolysis of $PCl_3$ to undesirable phosphorus acid, $H_3PO_3$, will occur.

The tertiary alkylphosphorodichloridite compounds produced by Reaction I are stable only at low temperatures, thus when reacting the alcohol and $PCl_3$ and purifying the product by distilling the excess phosphorous trichloride and solvent, the temperature must be kept below the decomposition temperature of the alkylphosphorodichloridites. The various alkylphorphorodichloridites which can be produced in accordance with Reaction I may have different decomposition temperatures depending on the chain length of the tertiary alcohol from which they were produced. It is contemplated that temperatures of about 0° C. or less will be suitable to prevent decomposition of the tertiary alkylphosphorodichloridites described herein. Particularly preferred are temperatures from about −40° C. to about 0° C., with temperatures in the range of from about −10° C. to about 0° C. being most particularly preferred.

The tertiary alkylphosphorodichloridite is recovered in a high state of purity and good yield by distillation at lowered pressures, i.e., in vacuo. That the distillation be conducted at temperatures lower than the decomposition temperature of the tertiary alkylphosphorodichloridite product has already been discussed. The product so purified must also be stored at low temperatures.

It is an object of the instant invention to utilize the tertiary alkylphosphorodichloridite compounds produced via Reaction I in the preparation of valuable disubstituted phosphorous acid compounds. These latter compounds are particularly useful as antiwear agents in lubricating media and may be produced via the following reaction scheme:

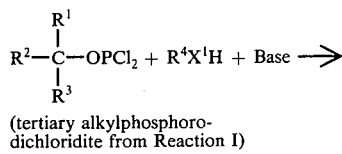

(tertiary alkylphosphoro-
dichloridite from Reaction I)

II

-continued

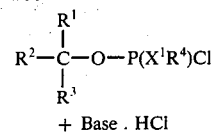

+ Base . HCl

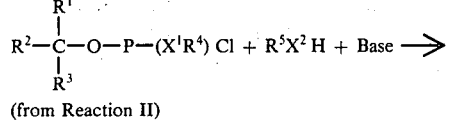

(from Reaction II)

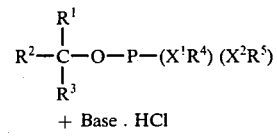

+ Base . HCl    IV

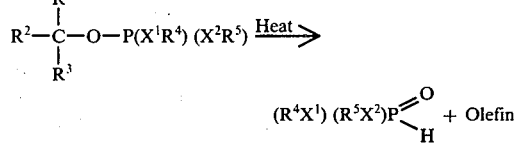

In the scheme illustrated above $R^4$ and $R^5$ may be alkyl, aryl or aralkyl. It is preferred that the groups be alkyl of from about 1 to about 40 carbon atoms, aryl of from about 6 to about 40 carbon atoms and aralkyl of from about 7 to about 40 carbon atoms.

Also, $X_1$ and $X_2$ may be chosen from the group consisting of O, S, N—$R^6$ where $R^6$ may be alkyl, aryl or aralkyl, especially those groups having chain length from about 1 to 40 carbon atoms. Particularly contemplated are $RX^-$ groups such as PhS—,

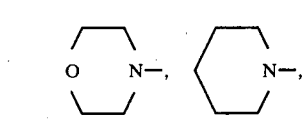

PhO—, RPhO—, RS—, $R_2N$ where Ph represents phenyl and R may be alkyl or aralkyl having from about 1 to about 40 carbon atoms.

The base may be described as a tertiary aliphatic or aromatic amine which has the formula:

where $R^A$, $R^B$ and $R^C$ are alkyl or aryl. Preferred are those amines where the alkyl or aryl groups contain from about 2 to about 16 carbon atoms. Amines in which the alkyl groups are cyclic are also contemplated. Additionally, pyridine and its derivatives, such as substituted pyridine; quinoline and its derivatives, such as substituted quinoline; and amines having the formula:

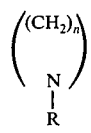

wherein n is 4 or 5 and R is alkyl or aryl containing from 1 to about 16 carbon atoms are suitable. Diethylaniline is particularly contemplated.

Reactions II and III depict replacing the chlorides of the tertiary alkylphosphorodichloridite, produced in Reaction I, with the $RX^-$ groups described above. The RX⁻ groups may be the same, in which case two moles of the RXH reactant would be used and Reactions II and III would occur simultaneously. Alternately, the RX⁻ groups may be different, and the reactions would occur sequentially as shown. One chlorine of the tertiary alkylphosphorodichloridite is replaced more rapidly than the other, thus allowing the reaction to stop after the addition of the first RX⁻ group. In this manner, the sequential addition of two different RX⁻ groups may be effected.

Reactions II and III are generally carried out at temperatures below the decomposition temperature of the tertiary alkylphosphorodichloridite as discussed for Reaction I. A suitable solvent such as pentane, petroleum ether, ethylether, benzene, toluene, hexane, mineral oils or other non-volatile solvents, if the ultimate use of the product will not be affected by the presence of these solvents, may be used.

In Reaction IV, the phosphite compound produced by Reactions II and III, i.e.,

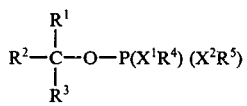

is gently heated. Normally, heating at temperatures from about 70° to about 170° C., preferably from about 90° to about 140° C., for about 0.4 to about 5 hours is enough to effect complete conversion of the substituted phosphite to disubstituted phosphorus acid compounds. The thermal liability of the original tertiary group, viz,

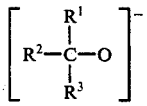

provides that it is preferentially removed before the subsequently added RX⁻ groups.

DESCRIPTION OF SPECIFIC EMBODIMENTS

The following non-limiting examples will serve to illustrate the invention:

EXAMPLE 1

Phosphorus trichloride (128.5 g) was distilled into 250 ml dry pentane, cooled to −5° C., and a mixture of diethylaniline (27.9 g) and t-butyl alcohol (13.9 g) in 30 ml pentane was added dropwise over 40 min. After 2 hours at 0° C., the solution was filtered in a water-free atmosphere into a distillation flask.

The PCl₃ and the solvent were removed, leaving 21.3 g (65% yield) of a product identified as t-butylphosphorodichloridite. The ³¹P NMR at 0° C. confirms the purity of this product by the presence of a single peak accounting for more than 98% of the phosphorus at −178.0 ppm.

Since (tBuo)PCl₂ is a new compound its ³¹P chemical shift is unknown but comparison of its chemical shift with the trends set forth in the Table below will show its value is as predicted from known compounds.

H₃PO₄ = 0.00 ppm
PCl₃ = −219 ppm

Values from "Topics in Phosphorus Chemistry, Vol. 5, ³¹P Nuclear Magnetic Resonance," M. M. Crutchfield et al., Interscience Publishers, New York, N.Y., 1967.

| R | ³¹P CHEMICAL SHIFT | | |
|---|---|---|---|
|   | P(OR)Cl₂ | P(OR)₂Cl | P(OR)₃ |
| Me | −180.5 | −169 | −141 |
| Et | −177.0 | −164.5 | −138.3 |
| iPn | −174.4 | −165.4 | −137.5 |
| tBu | — | −170.3 | −138.3 |

¹H NMR showed only a 0.56 Hz doublet at 1.61 ppm. The coupling constant is correct for a P—O—CC—H coupling as indicated by comparison with literature value for P—O—C—CH in (CH₃)₃C—OP—(NME)₂ given by R. Burgada et al., *Bull. Soc. Chem.* France, 1963, 2154.

EXAMPLE II

Phosphorus trichloride (129.3 g) was dissolved in 250 ml dry 35°–48° petroleum ether, cooled to −5° C., and a mixture of 28.0 g diethylaniline and 28.0 g 2-methyl-2-butanol in 50 ml petroleum ether added dropwise over 40 min. After 30 min. of stirring at −5° C. the mixture was filtered (excluding moisture) into a 1 liter flask. The volatile solvent and excess phosphorus trichloride were removed simply by lowering the pressure and keeping the distillation flask at 0°. The product of t-amyl phosporodichloridite weighed 23.5 g (72% yield) and was obtained in greater than 98% purity as shown by the presence of only one peak in its low temperature ³¹P NMR spectrum at −177 ppm.

EXAMPLE III t-butylphosphorodichloridite (9.32 g) from Example I was dissolved in 150 ml of 30°–60° petroleum either and cooled to 0° C. A solution of 23.4 g nonylphenol and 15.9 g diethylaniline was added over 30 min. After 5 hours at 0° C. the mixture was filtered in a moisture-free atmosphere. The solvent was distilled at atmospheric pressure (bp 45° C.) and removed completely at 40° C./0.05 mm. The product of bis-(4-nonylphenyl)-t-butyl phosphite is a colorless oil, 28.6 g (99% yield) was recovered.

EXAMPLE IV

The crude product of Example III, bis-(4-n-nonylphenyl)-t-butyl-phosphite, 28.6 g, was warmed to 95° C./1 mm at which point very rapid evolution of isobutylene took place. After 20 min. the product was cooled to give 25.6 g (100% yield) of a colorless oil, which had mp ≃ 5°. The purity and structure of the resulting product of bis-(4-n-nonylphenyl) phosphonate were established by elemental analysis and various NMR spectra.

ELEMENTAL ANALYSIS

Analysis calcd. for C₃₀H₄₇O₃P: C, 74.04%; H, 9.74%; P, 6.36% Found: C, 73.88%, H, 9.66%; P, 6.20%.

| ¹H NMR | Position | NMR SPECTRA | | |
|---|---|---|---|---|
|  |  | Description | Integration | Assignment |
|  | 7.20 ppm | d, J_{PH} = 725 Hz | 1.0 H | PH |
|  | 7.16 | S | 4.0 H | aromatic protons |
|  | 2.5 | t, J = 7 Hz | 2.0 H | R—CH₂Ar |

-continued

NMR SPECTRA

| | | | | |
|---|---|---|---|---|
| $^{13}$C NMR | 1.3–0.8 Position | envelope + t Remarks | 17.0 H | $CH_3(CH_2)_7-$ Assignment |
| | 147.5 ppm | d, $J_{POC}$ = 7.3 Hz | | C-1 |
| | 140.0 | | | C-4 |
| | 129.6 | | | C-3 and C-5 |
| | 120.3 | d, $J_{POC}$ = 4.3 Hz | | C-2 and C-6 |
| | 35.2, 32.0, 31.4, 29.6, 29.4, 29.3, 22.7 | | $-(CH_2)_8-$ | |
| | 14.1 | | | $CH_3$ |
| $^{31}$P NMR | Position | Remarks | | |
| | −0.41 ppm | $J_{P-H}$ = 724 Hz | | |

Chemical shifts are given as +ppm downfield of standard which was $(CH_3)_4Si$ for $^1H$ and $^{13}C$ NMR and +ppm upfield of standard which was 85% $H_3PO_4$ for $^{31}P$ NMR.

EXAMPLE V t-amylphosporodichloridite (24.3 g) from Example II was dissolved in 250 ml petroleum ether and cooled to −10° C. A solution of 38.3 g diethylaniline and 56.6 g nonylphenol in 150 ml petroleum ether was added over 1 hour. The mixture was allowed to stir overnight at room temperature, filtered (excluding moisture) and the solvent removed in vacuo. The product of bis-(4-nonylphenyl)-t-amylphosphite is a colorless oil, 62.6 g (87% yield) was recovered.

EXAMPLE VI

Crude product from Example V, was heated for 30 minutes at 100° C./0.3 mm Hg to give olefin (mostly 2-methyl-2-butene) plus bis-(4-nonylphenyl) phosphonate, 54.6 g (100% yield), as a colorless viscous oil whose purity and structure were established by its $^{31}$P NMR spectrum. The product contained 3% tris-(4-nonylphenyl) phosphite as its only detectable impurity.

ANTIWEAR ACTIVITY

Bis-(4-nonylphenyl) phosphonate, as prepared in accordance with Example VI, was added to a solvent refined paraffinic mineral oil base stock having a viscosity of 150 SUS at 210° F. and tested for antiwear activity using the Four Ball Wear Test. The concentration of the bis-(4-nonylphenyl) phosphonate was 0.1%, by weight. A complete description of the Four Ball Wear Test can be found in U.S. Pat. No. 3,423,316. In general, three steel balls of SAE 52-100 steel are held in a ball cup. A fourth ball, positioned on a rotatable verticle axis, is brought into contact with the three balls and is rotated against them. The force which the fourth ball is held against the three stationary balls is varied according to the desired load. The test lubricant is added to the ball cup and acts as a lubricant for the rotation. At the end of the test the steel balls are investigated for wear-scar; the extent of scarring represents the effectiveness of the lubricant as an antiwear agent. The conditions of the test were: 40 kg load, 600 rpm and 30 minutes test time; tests were made at both 200° F. and 400° F. Table 1 lists the test results.

TABLE 1

| 200° F Additive | Coefficient of Friction | Weat Scar Diameter | Wear Rate X $10^{12}$ cc/cm-Kg |
|---|---|---|---|
| Base oil | 0.0873 | 0.6858 | 4.6 |
| Base oil + .1 wt. % Bis-(4-nonylphenyl)-phosphonate | 0.0895 | 0.5671 | 2.3 |
| 400° F | | | |

TABLE 1-continued

| 200° F Additive | Coefficient of Friction | Weat Scar Diameter | Wear Rate X $10^{12}$ cc/cm-Kg |
|---|---|---|---|
| Base oil | 0.1593 | 0.8341 | 10.5 |
| Base oil + .1 wt. % Bis-(4-nonylphenyl)-phosphonate | 0.0832 | 0.6096 | 3.8 |

The test results reported in Table 1 show the efficacy of the compounds made in accordance with the invention as antiwear agents.

I claim:

1. A method which comprises reacting, at temperatures of 0° C. or less:
   (a) A tertiary alcohol having the formula:

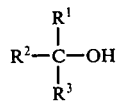

in which $R^1$, $R^2$ and $R^3$ are selected from the group consisting of alkyl having from about 1 to about 4 carbon atoms, aryl having from about 6 to about 8 carbon atoms, and aralkyl having from about 7 to about 10 carbon atoms, at least one being alkyl; with (b) a tertiary amine in a molar ratio of tertiary amine to tertiary alcohol of 1:1 or more; and
   (c) $PCl_3$ in an amount from about 1.25 to about 4 moles of $PCl_3$ per mole of alcohol, which amount is in excess of the stiochometric amount needed to react with the alcohol, wherein said alcohol is added slowly to said excess $PCl_3$;

and recovering, at temperatures of 0° C. or less, a tertiary alkyl phosphorodichloridite product.

2. The method in accordance with claim 1 wherein $R^1$, $R^2$ and $R^3$ are selected from the group consisting of methyl, ethyl, propyl, butyl and phenyl.

3. The method in accordance with claim 1 wherein said tertiary alcohol is selected from the group consisting of t-butanol, t-amyl alcohol, 3-methyl-3-hexane and 2-phenyl-2-propanol.

4. The method in accordance with claim 1 wherein said tertiary amine has the formula:

in which $R^A$, $R^B$ and $R^C$ are alkyl and aryl groups which contain from about 2 to about 16 carbon atoms.

5. The method in accordance with claim 1 wherein said tertiary amine is selected from the group consisting of pyridine, quinoline and derivatives thereof.

6. The method in accordance with claim 1 wherein said tertiary amine is diethylaniline.

* * * * *

UNITED STATES PATENT AND TRADEMARK OFFICE
CERTIFICATE OF CORRECTION

PATENT NO. : 4,120,917
DATED : October 17, 1978
INVENTOR(S) : KIRK D. SCHMITT

It is certified that error appears in the above-identified patent and that said Letters Patent are hereby corrected as shown below:

Column 7, line 9, "$-(CH_2)8-$" should be under "Assignment" instead of under "Remarks."
Column 7, line 64, "Weat Scar" should read --Wear Scar--.
Column 8, line 16, "Weat Scar" should read --Wear Scar--.
Column 7, line 69, delete 400°F
Column 8, line 15, "200°F" should read --400°F--.

Signed and Sealed this

Thirteenth Day of March 1979

[SEAL]

Attest:

RUTH C. MASON
Attesting Officer

DONALD W. BANNER
Commissioner of Patents and Trademarks